(12) United States Patent
Burns

(10) Patent No.: US 6,569,181 B1
(45) Date of Patent: May 27, 2003

(54) STENT RETRIEVAL SYSTEM

(75) Inventor: Denise H. Burns, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 224 days.

(21) Appl. No.: 09/745,254

(22) Filed: Dec. 20, 2000

(51) Int. Cl.$^7$ ................................................ A61F 11/00
(52) U.S. Cl. ...................................... 606/198; 606/108
(58) Field of Search ................................ 606/198, 200, 606/181, 108, 192, 195, 194, 151, 152, 153, 154, 155, 156

(56) References Cited

U.S. PATENT DOCUMENTS

| | | |
|---|---|---|
| 5,035,706 A | 7/1991 | Giantureo et al. |
| 5,330,482 A | 7/1994 | Gibbs et al. |
| 5,411,549 A | 5/1995 | Peters |
| 5,474,563 A | 12/1995 | Myler et al. |
| 5,624,450 A | 4/1997 | Glastra |
| 5,649,906 A | 7/1997 | Gory et al. |
| 5,713,948 A | 2/1998 | Uflacker |
| 5,716,410 A | 2/1998 | Wang et al. |
| 5,733,302 A | 3/1998 | Myler et al. |
| 5,776,186 A | 7/1998 | Uflacker |
| 5,833,707 A | 11/1998 | McIntyre et al. |
| 5,868,753 A * | 2/1999 | Schatz ..................... 606/108 |
| 5,882,335 A | 3/1999 | Leone et al. |
| 5,976,172 A | 11/1999 | Homsma et al. |
| 6,027,508 A | 2/2000 | Ren et al. |
| 6,077,298 A | 6/2000 | Tu et al. |
| 6,221,096 B1 | 4/2001 | Aiba et al. |
| 2002/0026230 A1 | 2/2002 | Moll et al. |

* cited by examiner

Primary Examiner—David J. Isabella
(74) Attorney, Agent, or Firm—Fulwider Patton Lee & Utecht, LLP

(57) ABSTRACT

The invention is directed to a stent retrieval method and system which generally includes an elongated retrieval catheter having an inner member and an outer member and a collapsible tube. A manipulating device is provided on the proximal end of the system to effect relative axial movement between the inner and outer members to collapse the tube around the sent and retrieve the stent from a vessel such as a coronary artery.

11 Claims, 4 Drawing Sheets

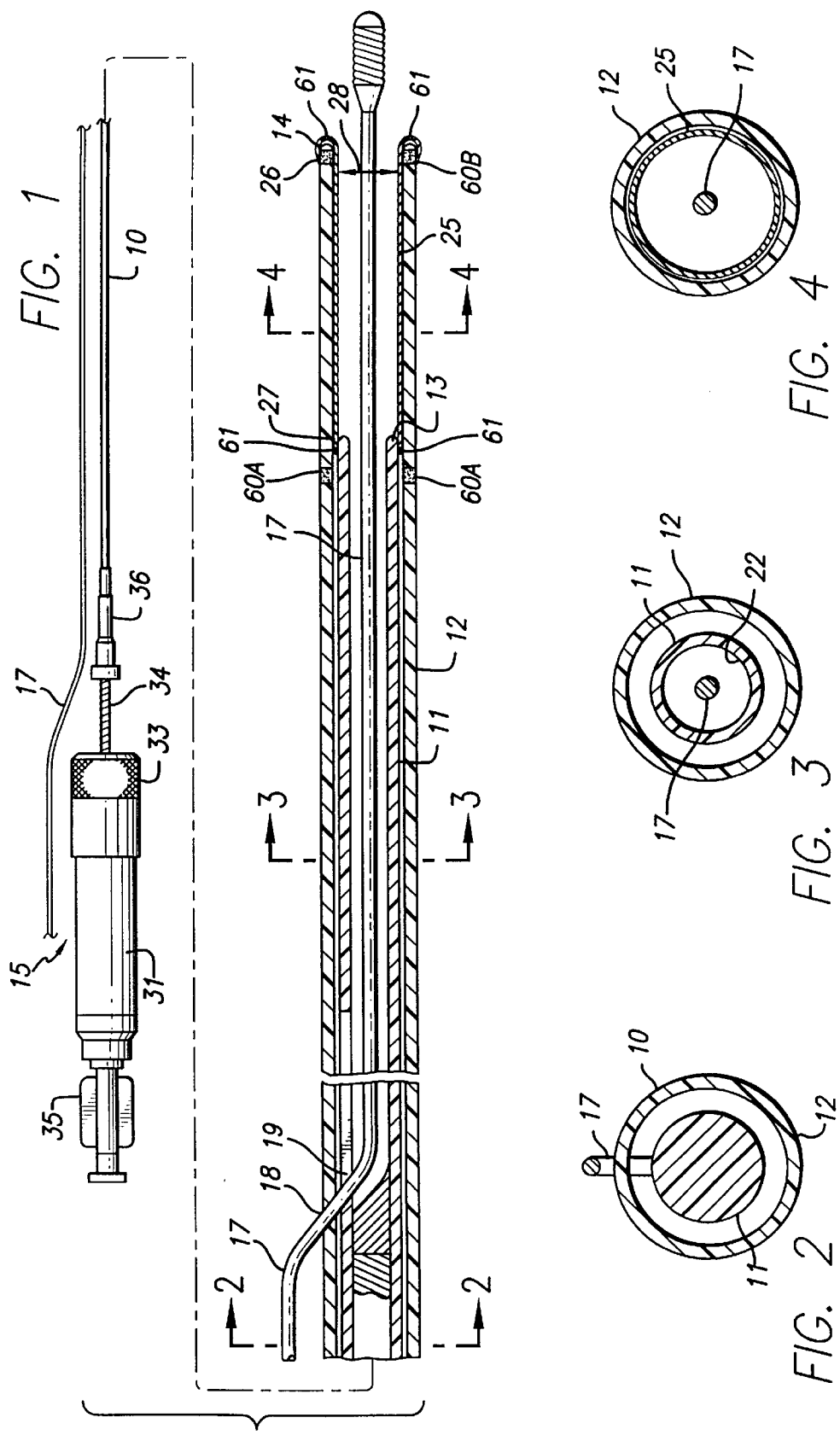

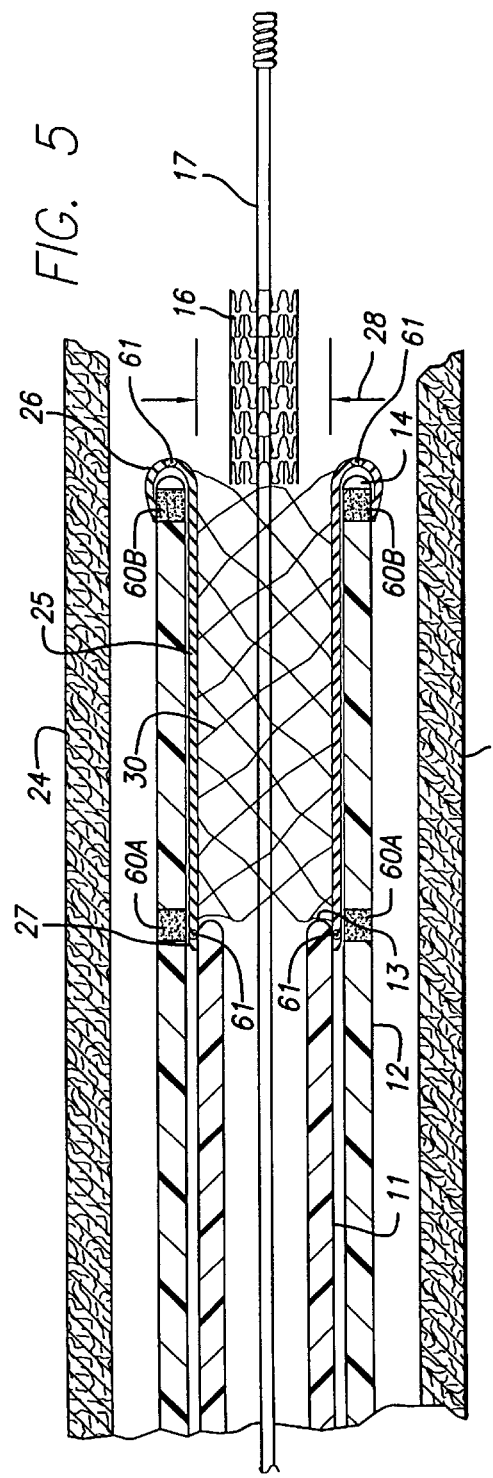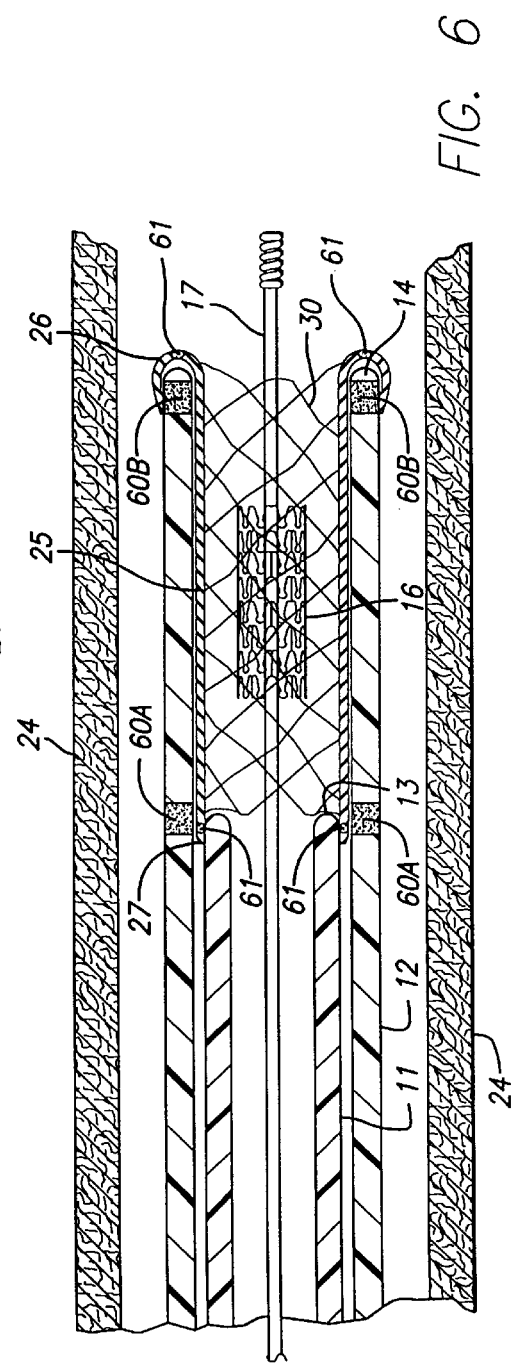

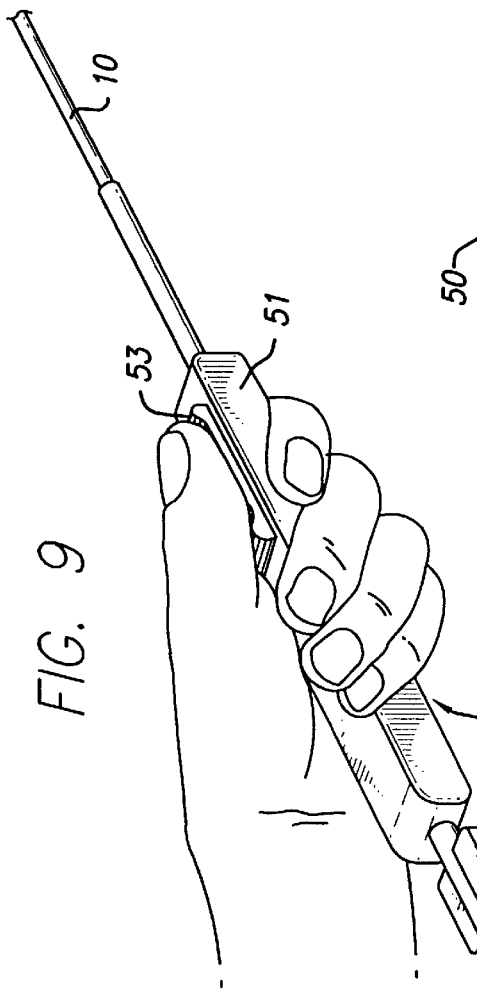
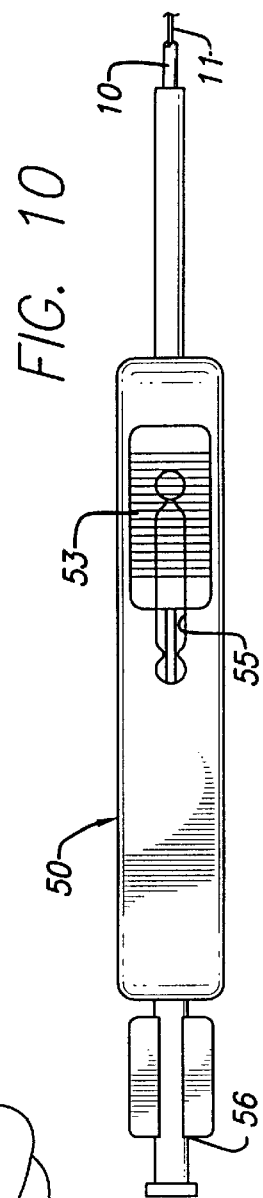
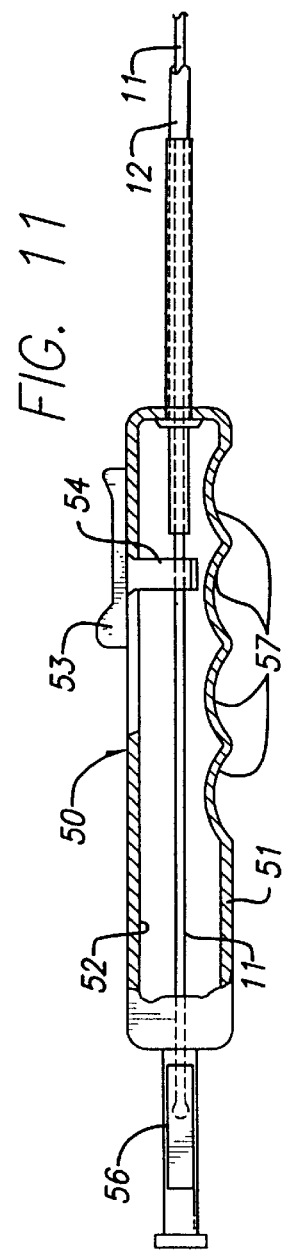

STENT RETRIEVAL SYSTEM

BACKGROUND OF THE INVENTION

This invention relates to devices for the treatment of heart disease and particularly to endow-arterial prostheses which are commonly called stints. More particularly, a catheter assembly is configured to retrieve a stent or other object from a vessel.

Several interventional treatment modalities are presently used for heart disease including balloon and laser angioplasty, atherectomy and by-pass surgery. In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium of a desired coronary artery. A guide wire is positioned within an inner lumen of a dilatation catheter and then both are advanced through the guiding catheter to the distal end thereof. The guide wire is first advanced out of the distal end of the guiding catheter into the patient's coronary vasculature until the distal end of the guide wire crosses a lesion to be dilated. Then the dilatation catheter having an inflatable balloon on the distal portion thereof is advanced into the patient's coronary anatomy over the previously introduced guide wire until the balloon of the dilatation catheter is properly positioned across the lesion. Once in position across the lesion, the balloon which is made of relatively inelastic materials, is inflated to a predetermined size with radiopaque liquid at relatively high pressure (e.g., greater than 4 atmospheres) to press the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guide wires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson et al.); U.S. Pat. No. 4,554,929 (Samson et al.); U.S. Pat. No. 4,616,652 (Simpson); U.S. Pat. No. 4,638,805 (Powell); and U.S. Pat. No. 4,748,982 (Horzewski etal.) which are hereby incorporated herein in their entirety by reference thereto.

One problem characteristic of balloon angioplasty procedures is the large number of patients who are subject to restenosis in the treated artery. In the case of restenosis, the treated artery may again be subjected to balloon angioplasty or to other treatments such as by-pass surgery if additional balloon angioplasty procedures are not warranted. However, in the event of a partial or total occlusion of a coronary artery by the collapse of a dissected arterial lining after the balloon is deflated, the patient is put in a situation requiring immediate medical attention, particularly in the coronary arteries.

A major focus of recent development work in the treatment of heart disease has been directed to endoprosthetic devices called stents. Stents are generally cylindrically shaped intravascular devices which are placed within a damaged artery to hold it open. The device can be used to prevent restenosis and to maintain the patency of blood vessels immediately after intravascular treatments. In some circumstances, they can also be used as the primary treatment device where they are expanded to dilate a stenosis and then left in place.

Two basic methods and systems have been developed for delivering stents to desired locations within body lumens. One method and system involves compressing or otherwise reducing the diameter of an expandable stent, disposing the compressed stent within a lumen provided in the distal end of a tubular catheter, advancing the catheter through the patient's vasculature until the distal end of the catheter is immediately adjacent to the desired vascular location, and then pushing the stent out the distal end of the catheter into the desired location. Once out of the catheter, the compressed stent expands or is expanded to thereby hold open the artery or other body lumen into which it is placed.

Another method and system involves disposing a compressed or otherwise small diameter stent about an expandable member such as a balloon on the distal end of a catheter, advancing the catheter through the patient's vascular system until the stent is in the desired location within a blood vessel and then expanding the expandable member on the catheter to expand the stent within the blood vessel. The expanded expandable member is then contracted and the catheter withdrawn, leaving the expanded stent within the blood vessel, holding open the passageway thereof.

Occasionally, a stent comes off of the catheter prior to expansion in the vessel, thereby embolizing in the vessel with no way to retrieve it. Likewise, a partially expanded stent may not stay expanded in the vessel and embolize. Other devices, such as embolic filters and the like, also may prematurely be dislodged from their delivery systems. In such cases, it is important to retrieve the stent or filter in order to reduce the likelihood of injury to the patient. Thus far, prior art devices have been unsuccessful in reliably locating and retrieving stents or filters for removal from the patient's vascular system.

The prestent invention catheter retrieval system is configured for locating and reliably retrieving a stent or filter from a patient's vascular system without injury to the patient.

SUMMARY OF THE INVENTION

The prestent invention provides for a reliable and safe apparatus and method for capturing and retrieving a stent, filter, or other device that has embolized in a patient's vascular system. The prestent invention provides for an intravascular catheter having an inner member disposed within an outer member and having relative axial movement between the inner member and the outer member. A manipulating device or handle, operated by the physician, provides the relative axial movement between the inner member and the outer member. Disposed at the distal end of the inner member is a tube, such as a mesh braid, that is attached to the distal end of the inner member. The other end of the tube is attached to the distal end of the outer member. When the inner member is withdrawn proximally by the physician operating the manipulator, or handle, the tube reduces in size from a first enlarged diameter to a second compressed diameter.

The tube can be a typical mesh braid or similar mesh pattern made of stainless steel, nickel-titanium alloys, Elgiloy, or a polymer. The proximal end of a tube is attached to the distal end of the inner member by an adhesive, laser welding, or the like. Likewise, the distal end of the tube is preferably wrapped around the outside of the distal end of the outer member and attached by an adhesive, laser welding, or similar attachment means.

In the method of using the invention, the catheter, preferably a catheter of the rapid-exchange type, is advanced over a previously positioned guide wire. The guide wire preferably is threaded through the stent or filter that has embolized in the patient's vascular system. As the catheter is advanced, the distal end of the outer member and the tube are advanced over the stent or filter. In order to capture the stent, the inner member is then withdrawn proximally by the physician operating the manipulator in order to cause the tube to compress from its first expanded diameter to its second compressed diameter. As the tube collapses, it tightly grips the stent or filter so that the stent is captured and can be removed from the patient. The catheter assembly and guide wire are withdrawn from the patient, or if another procedure is required, the guide wire can be left in the patient's vascular system and the catheter removed in a rapid-exchange manner. Alternatively, over-the-wire or other similar catheter systems can be used with the prestent invention.

BRIEF DESCRIPTION OF THE DRAWINGS

FIG. 1 is a partial longitudinal cross-sectional view of a stent retrieval system which embodies features of the invention.

FIG. 2 is a cross-sectional view taken along lines 2—2 depicting the rapid exchange feature of the stent retrieval catheter.

FIG. 3 is a cross-sectional view taken along lines 3—3 depicting the outer and inner members.

FIG. 4 is a cross-sectional view taken along lines 4—4 depicting the outer member and the retrieval tube.

FIG. 5 is a partial longitudinal cross-sectional view depicting the advancement of the stent retrieval system shown in FIG. 1 into an artery FIG. 6 is a partial longitudinal cross-sectional view depicting the stent retrieval system positioned so that the retrieval tube covers the stent.

FIG. 9 is a perspective view of an alternative manipulator mounted on the proximal end of the delivery system shown in FIG. 1.

FIG. 10 is a plan view of the manipulator shown in FIG. 9.

FIG. 11 is an elevational view, partially in section, of the manipulator shown in FIG. 9.

DETAILED DESCRIPTION OF THE PREFERRED EMBODIMENTS

Figure 7:
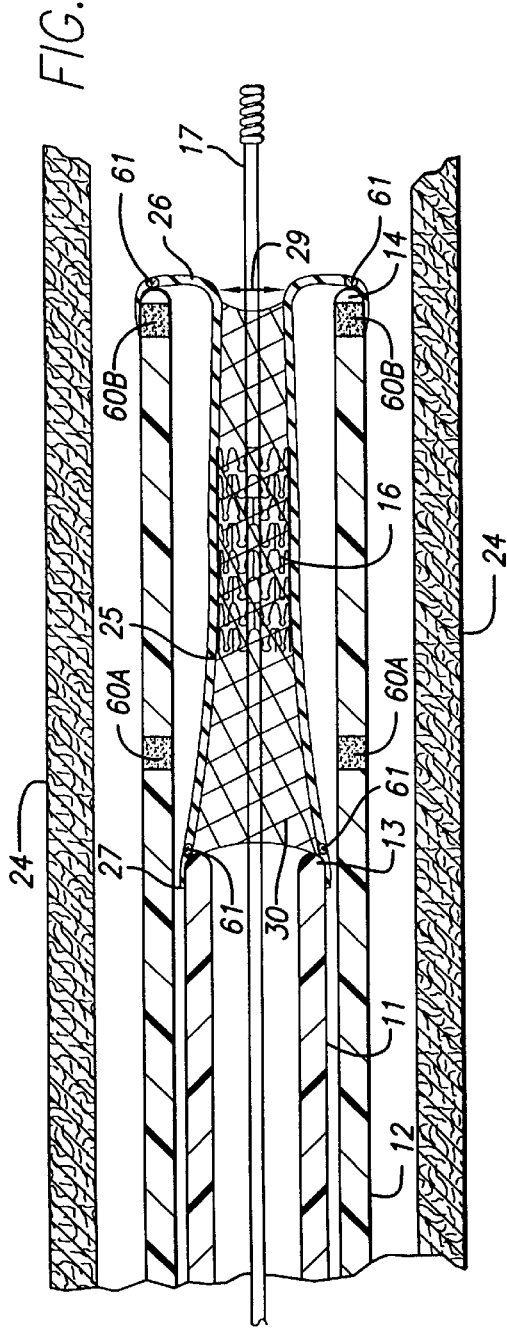
FIG. 7 is a partial longitudinal cross-sectional view depicting the stent retrieval system where the retrieval tube has been collapsed to capture the stent.

The prestent invention relates generally to a catheter retrieval system for removing objects from body lumens, such as removal of stents, filters, or other objects from body lumens such as coronary arteries, carotid arteries, peripheral arteries, veins, esophageal tubes, urethral tubes, biliary tube, and the like. The catheter retrieval system will locate and safely remove an object from a body lumen without any injury to the patient in a safe and efficient manner.

In keeping with one aspect of the invention, as shown in FIGS. 1–7, a catheter 10 includes an inner member 11 and an outer member 12. The inner member is disposed for slidable movement within the outer member and the inner member is slightly shorter than the outer member. A manipulator 15, located at the proximal end of the catheter, is used to impart relative axial movement between the inner member and the outer member. As shown in FIG. 1, the catheter is configured in the rapid-exchange configuration, in which a guide wire 17 exits the catheter through a port 18 that is relatively closer to the catheter distal end than the catheter proximal end. For example, typically proximal port 18 can be located anywhere from 2 to 40 cm from the distal end of the catheter. The inner member also has a proximal port 19 that coincides with the proximal port 18 in the outer member. The proximal port 19 is more in the form of a slot since the inner member will be withdrawn proximally relative to the outer member as herein described. An inner lumen 22 is sized for slidably receiving the guide wire 17. Alternatively, the catheter 10 can be configured in the known over-the-wire design for use with the prestent invention.

A retrieval tube 25 is disposed within the distal end of the outer member 12 for capturing and retrieving a stent, filter, or other device or emboli in a body lumen. The retrieval tube has a distal end 26 that is attached to the distal end 14 of the outer member 12, and the tube has a proximal end 27 that is attached to the distal end 13 of the inner member 11. Attachment can be by any convenient means including use of adhesives that are well known in the art, welding, or laser welding. In one embodiment, the distal end 26 of the retrieval tube is wrapped around the distal end 14 of the outer member to provide a bigger opening for capturing the stent, filter or the like. The retrieval tube has an open diameter 28 as shown in FIG. 1, and a collapsed diameter 29 as shown in FIG. 7. The collapsed diameter of the retrieval tube should correspond to the size of the object being retrieved, such as an intravascular stent or filter. The open diameter obviously must be large enough to surround and capture the stent or filter.

The retrieval tube 25 is formed of a lattice-like structure that is capable of easily collapsing from the open diameter to the collapsed diameter upon lengthening of the tube. For example, interlaced strands 30 or wirelike ribbons (flat ribbons) that are in the form of spirals or helixes are suitable for the tube structure. Further, a mesh having diamond-shaped criss-crosses also would be suitable. The retrieval tube can be formed of metals or metal alloys, or can be formed from polymer materials. For example, the retrieval tube can be formed from stainless steel, nickel-titanium, tantalum, cobalt chromium, Elgiloy or other similar materials that will easily collapse upon lengthening of the tube from the open diameter 28 to the collapsed diameter 29. Similarly, the retrieval tube can be formed of a polymer material including polyurethanes, polyethylene, polyethylene terephthalate, nylons, and the like.

Figure 8:
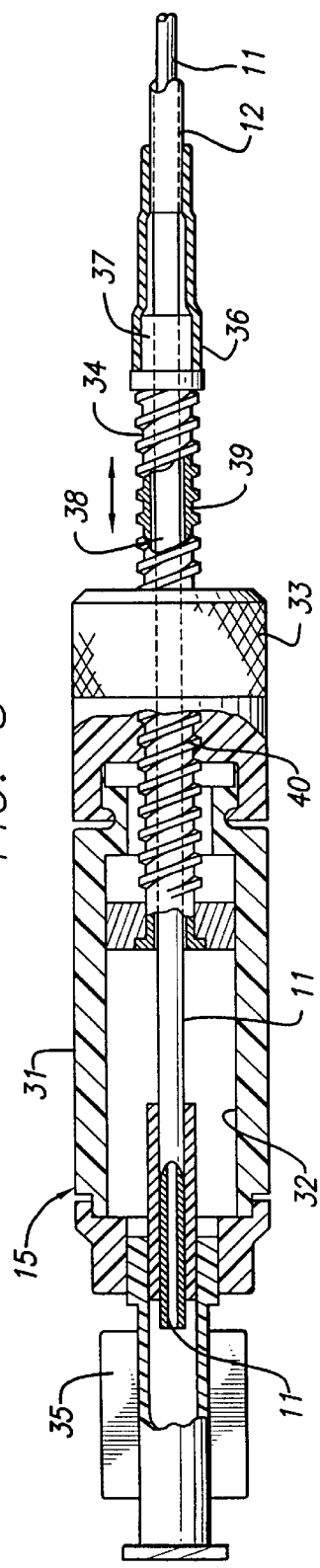
FIG. 8 is a partial cross-sectional view of the manipulator shown in FIG. 1.

As shown in FIGS. 1 and 8, a manipulator 15 is used to impart axial movement between the inner member 11 and the outer member 12. Since the retrieval tube 25 is attached at its distal end 26 to the distal end 14 of the outer member, and attached at its proximal end 27 to the distal end 13 of the inner member 11, when the inner member is retracted proximally by the manipulator, the retrieval tube will lengthen and it will collapse from its open diameter 28 configuration to its collapsed diameter 29 configuration. Due to the lattice nature of the retrieval tube, the wires or wirelike strands 30 making up the tube will slide over each other as the tube gets smaller in diameter.

As illustrated in FIGS. 1 and 8, the manipulator 15 on the proximal end of the retrieval system has a housing 31 with an interior chamber 32, a cap 33 rotatably mounted onto the distal end of the housing, an elongated drive member 34 which has male threads on the exterior thereof and which is at least partially disposed within the interior chamber 32, and a Luer lock 35 which is fixed within the proximal end of the housing. The proximal end 36 of the inner member 11 is secured to the distal end 37 of the elongated drive member 34 which extends out of the distal end of the housing. As shown in more detail FIG. 8, the proximal end 38 of the outer member 12 passes through passageway 39 in the elongated drive member and is fixed within the Luer lock 35 by suitable means such as adhesive. The cap which is rotatably mounted onto the distal end of the housing is provided with an inner threaded collar 40 adapted to threadably engage the threaded exterior of the elongated driving member. Rotation of the cap moves the driving member axially to thereby effect axial movement of the inner member 11 and relative axial movement between the inner member and the outer member 12. The outer member 12 overlies the inner member 11, such that there is little or no contact prestent at the interface of the two members so that the relative axial movement is virtually frictionless.

The inner member 11 is preferably positioned within the outer member 12 so that at least a significant portion of the proximal port 18 in the outer member is in alignment with the proximal port 19 of the inner member. In this manner, proximal advancement of the guide wire 17 through the inner lumen 22 will also direct the proximal end of the guide wire out the proximal port 18 in the outer member. The proximal end of the guide wire may then be manually held to maintain the position of the guide wire within the patient's vasculature while the stent retrieval system is advanced over the guide wire and through the patient's vascular system. Next, the manipulator 15 on the proximal end of the delivery system is actuated by rotating the cap 33 on the proximal end of the housing 31 to move the inner member 11 proximally with respect to the outer member. The retrieval system may then be removed from the patient along with the guide wire 17, removing the stent 16 from the arterial section as shown in FIGS. 6 and 7.

The housing 31 of the manipulator 15 can be held in the palm of the physician's hand, with the thumb and index finger thereof used to rotate cap 33 and thereby cause the necessary relative motion between the inner member 11 and the outer member 12 to collapse the retrieval tube 25 over the stent. The entire assembly, including the guide wire 17, can then be removed from the patient.

An alternative manipulator 50, illustrated in FIGS. 9–11, generally includes a housing 51 with an interior chamber 52 and a slidable element 53 with a depending portion 54 which extends through a slot 55 in the wall of the housing and is secured to the proximal end of the inner member or which extends through an opening provided in the distal end of the housing. As is evident from FIG. 11, movement from element 53 on the exterior of the housing 51 will effect the relative axial movement between the inner member 11 and the outer member 12 to collapse the tube 25 over the stent. The slot 55 has narrowed portions near both ends thereof which have widths just slightly smaller than the depending element 54 so that the position of the slidable element 53 can be locked. The underside of the housing 51 may be provided with undulated surface 57 which is adapted to receive the fingers of an operator to facilitate the gripping thereof.

Both the manipulator 15 and alternative manipulator 50 are indexed to provide the physician with the diameter of the retrieval tube 25 as the tube is collapsed from its open diameter 28 to the collapsed diameter 29. For example, each indexed rotation or slidable movement of the manipulators 15,50 respectively, corresponds to a specific diameter of the retrieval tube. This will assist the physician in determining how far to turn the cap 33 or move the slidable element 53 when reducing the diameter of the tube. Presumably, the physician will know the size of the object to be retrieved, such as an intravascular stent for coronary applications having a length, for example, 15 mm and a diameter of approximately 2 mm. In certain circumstances, however, the physician may not be able to determine the exact size of the object to be retrieved, making the indexing an added benefit.

A further benefit of the invention to help locate and retrieve stents and the like, are radiopaque markers associated with the stent retrieval system. More specifically, the outer member 12 has radiopaque markers 60A and 60B which coincide with the length of the retrieval tube 25 when it is in its open diameter 28 configuration. Thus, as seen in FIG. 1, radiopaque marker 60A coincides with the proximal end 27 of the retrieval tube and radiopaque marker 60B positioned at the distal end 14 of the outer member coincides with the distal end 26 of the tube. Alternatively, the retrieval tube can have radiopaque markers 61 defining its distal and proximal ends.

The dimensions of the catheter will generally follow the dimensions of intravascular catheters used in angioplasty procedures in the same arterial location. Typically, the length of a catheter for use in the coronary arteries is about 150 cm, and the outer diameter of the outer member 12 is about 0.035 inch (0.89 mm).

The materials of construction may be selected from those used in conventional balloon angioplasty catheters, such as those described in the patents incorporated by reference. The inner and outer members can be made of conventional tubing made from fluorinated ethylene-propylene resins (FEP), polytetrafluoroethylene (PTFE), fluoropolymers (Teflon), polyethylene terephthalate (PET), hytrel polyesters, aromatic polymers, polyetherketones (PEEK), polyamidl/polyester block copolymers having a tensile strength of at least 6,000 psi and an elongation of at least 300%, polyamids, nylon materials, or nylon 12 having a tensile strength of at least 15,000 psi, or other suitable material that may be developed.

While the prestent invention has been described herein in terms of removing a stent or filter from within a patient's blood vessel, the system can be employed to remove stents, filters, or other objects from within other body lumens. Various changes and improvements may also be made to the invention without departing from the scope thereof.

What is claimed:

1. A catheter assembly for removing an object from a body lumen, comprising:
    a catheter having a proximal end and a distal end, the catheter also having an inner member slidably disposed within an outer member;
    a retrieval tube disposed within a distal end of the outer member, the tube having a distal end attached to a distal end of the outer member and a proximal end attached to a distal end of the inner member, the tube having an open diameter and collapsed diameter;
    whereby the inner member is withdrawn proximally relative to the outer member so that the tube lengthens and compresses from the open diameter to the collapsed diameter.

2. The assembly of claim 1, wherein the retrieval tube is formed of a lattice structure.

3. The assembly of claim 2, wherein the lattice structure includes a plurality of strands that slide over each other as the retrieval tube compresses from the open diameter to the collapsed diameter.

4. The assembly of claim 1, wherein the retrieval tube is formed from a metal alloy taken from the group of metal alloys consisting of stainless steel, nickel titanium, titanium, tantalum and cobalt-chromium.

5. The assembly of claim 1, wherein the retrieval tube is formed from a polymer taken from the group of polymers consisting of polyethylene, polyurethane, polyethylene terephthalate (PET), fluorinated ethylene-propylene resins (FEP), polytetrafluoroethylene (PTFE), fluoropolymers (Teflon), hytrel polyesters, aromatic polymers, polyetherketones (PEEK), polyamid/polyester block copolymers having a tensile strength of at least 6,000 psi and an elongation of at least 300%, polyamids, nylon materials, or nylon 12 having a tensile strength of at least 15,000 psi.

6. The assembly of claim 1, wherein the distal end of the tube is attached to the distal end of the outer member by an adhesive and the proximal end of the tube is attached at the distal end of the inner member by an adhesive.

7. The assembly of claim 1, wherein the distal end of the retrieval tube is attached to the distal end of the outer member by a laser weld and the proximal end of the tube is attached to the distal end of the inner member by a laser weld.

8. The assembly of claim 1, further comprising a manipulator to impart relative movement between the inner member and the outer member by proximally withdrawing the inner member.

9. The assembly of claim 1, wherein the catheter is a rapid-exchange catheter, the inner member and outer member each comprising a guide wire port.

10. A method for removing an object from a body lumen, comprising:
   providing a catheter assembly having an inner member slidably disposed within an outer member, a retrieval tube disposed within the distal end of the outer member, the tube having a distal end attached to a distal end of the outer member and a proximal end attached to a distal end of the inner member, the tube having an open diameter and a closed diameter;
   advancing the catheter assembly over a guide wire to desired location within the body lumen;
   advancing the assembly so that the retrieval tube is positioned over the object to be retrieved;
   withdrawing proximally the inner tube so that the retrieval tube compresses from the open diameter to the collapsed diameter to capture the object; and
   withdrawing the assembly from the body lumen over the guide wire.

11. The method of claim 10, wherein the retrieval tube has strands that slide over each other as the tube lengthens and the diameter lessens from the open diameter to the collapsed diameter.

* * * * *